United States Patent
Li (10) Patent No.: US 11,464,627 B2
(45) Date of Patent: Oct. 11, 2022

(54) STENT AND IMPLANTABLE VALVE INCORPORATING SAME

(71) Applicant: St. Jude Medical, Cardiology Division, Inc., St. Paul, MN (US)

(72) Inventor: XueMei Li, Shoreview, MN (US)

(73) Assignee: St. Jude Medical, Cardiology Division, Inc., St. Paul, MN (US)

(*) Notice: Subject to any disclaimer, the term of this patent is extended or adjusted under 35 U.S.C. 154(b) by 1120 days.

(21) Appl. No.: 15/988,695

(22) Filed: May 24, 2018

(65) Prior Publication Data

US 2018/0263770 A1    Sep. 20, 2018

Related U.S. Application Data

(62) Division of application No. 13/796,350, filed on Mar. 12, 2013, now Pat. No. 10,004,597.

(60) Provisional application No. 61/667,487, filed on Jul. 3, 2012.

(51) Int. Cl.
*A61F 2/24* (2006.01)

(52) U.S. Cl.
CPC .......... *A61F 2/2418* (2013.01); *A61F 2/2415* (2013.01); *A61F 2220/005* (2013.01); *A61F 2220/0058* (2013.01)

(58) Field of Classification Search
CPC .................. A61F 2/2418; A61F 2/2415; A61F 2220/005; A61F 2220/0058
See application file for complete search history.

(56) References Cited

U.S. PATENT DOCUMENTS

| | | | |
|---|---|---|---|
| 3,657,744 | A | 4/1972 | Ersek |
| 4,275,469 | A | 6/1981 | Gabbay |
| 4,491,986 | A | 1/1985 | Gabbay |
| 4,759,758 | A | 7/1988 | Gabbay |
| 4,878,906 | A | 11/1989 | Lindemann et al. |
| 4,922,905 | A | 5/1990 | Strecker |
| 4,994,077 | A | 2/1991 | Dobben |
| 5,411,552 | A | 5/1995 | Andersen et al. |

(Continued)

FOREIGN PATENT DOCUMENTS

| | | |
|---|---|---|
| DE | 19857887 B4 | 5/2005 |
| DE | 10121210 B4 | 11/2005 |

(Continued)

OTHER PUBLICATIONS

Li, X.M., U.S. Appl. No. 61/512,999, filed Jul. 29, 2011.

(Continued)

*Primary Examiner* — Jerrah Edwards
*Assistant Examiner* — Rokhaya Diop
(74) *Attorney, Agent, or Firm* — Wei & Sleman LLP (57) ABSTRACT

A collapsible stent for an implantable prosthetic valve incorporates leaflet-supporting members having relatively large surface area in comparison to other members defining the remainder of the stent. The leaflet-supporting members may have openings extending through them. The valve leaflets may be attached to the stent so that an attached edge of each leaflet extends along the leaflet-supporting members and is attached to the members by polymer integral with the leaflet overlying the leaflet supporting members and extending into the openings of the leaflet supporting members. The secure attachment resists stress on the leaflets.

20 Claims, 8 Drawing Sheets

(56) References Cited

U.S. PATENT DOCUMENTS

| | | | |
|---|---|---|---|
| 5,480,423 A | 1/1996 | Ravenscroft et al. | |
| 5,843,167 A | 12/1998 | Dwyer et al. | |
| 5,855,601 A | 1/1999 | Bessler et al. | |
| 5,935,163 A | 8/1999 | Gabbay | |
| 5,961,549 A | 10/1999 | Nguyen et al. | |
| 6,077,297 A | 6/2000 | Robinson et al. | |
| 6,083,257 A | 7/2000 | Taylor et al. | |
| 6,090,140 A | 7/2000 | Gabbay | |
| 6,214,036 B1 | 4/2001 | Letendre et al. | |
| 6,264,691 B1 | 7/2001 | Gabbay | |
| 6,267,783 B1 | 7/2001 | Letendre et al. | |
| 6,368,348 B1 | 4/2002 | Gabbay | |
| 6,419,695 B1 | 7/2002 | Gabbay | |
| 6,468,660 B2 | 10/2002 | Ogle et al. | |
| 6,488,702 B1 | 12/2002 | Besselink | |
| 6,517,576 B2 | 2/2003 | Gabbay | |
| 6,533,810 B2 | 3/2003 | Hankh et al. | |
| 6,582,464 B2 | 6/2003 | Gabbay | |
| 6,610,088 B1 | 8/2003 | Gabbay | |
| 6,623,518 B2 | 9/2003 | Thompson et al. | |
| 6,685,625 B2 | 2/2004 | Gabbay | |
| 6,719,789 B2 | 4/2004 | Cox | |
| 6,730,118 B2 | 5/2004 | Spenser et al. | |
| 6,783,556 B1 | 8/2004 | Gabbay | |
| 6,790,230 B2 | 9/2004 | Beyersdorf et al. | |
| 6,814,746 B2 | 11/2004 | Thompson et al. | |
| 6,830,584 B1 | 12/2004 | Seguin | |
| 6,869,444 B2 | 3/2005 | Gabbay | |
| 6,893,460 B2 | 5/2005 | Spenser et al. | |
| 6,908,481 B2 | 6/2005 | Cribier | |
| 6,953,332 B1 * | 10/2005 | Kurk | A61F 2/2415 249/52 |
| 7,018,406 B2 | 3/2006 | Seguin et al. | |
| 7,025,780 B2 | 4/2006 | Gabbay | |
| 7,137,184 B2 | 11/2006 | Schreck | |
| 7,160,322 B2 | 1/2007 | Gabbay | |
| 7,247,167 B2 | 7/2007 | Gabbay | |
| 7,267,686 B2 | 9/2007 | DiMatteo et al. | |
| 7,311,730 B2 | 12/2007 | Gabbay | |
| 7,374,573 B2 | 5/2008 | Gabbay | |
| 7,381,218 B2 | 6/2008 | Schreck | |
| 7,452,371 B2 | 11/2008 | Pavcnik et al. | |
| 7,510,572 B2 | 3/2009 | Gabbay | |
| 7,524,331 B2 | 4/2009 | Birdsall | |
| RE40,816 E | 6/2009 | Taylor et al. | |
| 7,585,321 B2 | 9/2009 | Cribier | |
| 7,682,389 B2 | 3/2010 | Beith | |
| 7,682,390 B2 | 3/2010 | Seguin | |
| 7,731,742 B2 | 6/2010 | Schlick et al. | |
| 7,803,185 B2 | 9/2010 | Gabbay | |
| 7,846,203 B2 | 12/2010 | Cribier | |
| 7,846,204 B2 | 12/2010 | Letac et al. | |
| 7,914,569 B2 | 3/2011 | Nguyen et al. | |
| D648,854 S | 11/2011 | Braido | |
| D652,926 S | 1/2012 | Braido | |
| D652,927 S | 1/2012 | Braido et al. | |
| D653,341 S | 1/2012 | Braido et al. | |
| D653,342 S | 1/2012 | Braido et al. | |
| D653,343 S | 1/2012 | Ness et al. | |
| D654,169 S | 2/2012 | Braido | |
| D654,170 S | 2/2012 | Braido et al. | |
| D660,432 S | 5/2012 | Braido | |
| D660,433 S | 5/2012 | Braido et al. | |
| D660,967 S | 5/2012 | Braido et al. | |
| D684,692 S | 6/2013 | Braido | |
| 2002/0036220 A1 | 3/2002 | Gabbay | |
| 2002/0173842 A1 | 11/2002 | Buchanan | |
| 2003/0023303 A1 | 1/2003 | Palmaz et al. | |
| 2003/0050694 A1 | 3/2003 | Yang et al. | |
| 2003/0130726 A1 | 7/2003 | Thorpe et al. | |
| 2004/0049262 A1 | 3/2004 | Obermiller et al. | |
| 2004/0093075 A1 | 5/2004 | Kuehne | |
| 2004/0210304 A1 | 10/2004 | Seguin et al. | |
| 2005/0096726 A1 | 5/2005 | Sequin et al. | |
| 2005/0137681 A1 | 6/2005 | Shoemaker et al. | |
| 2005/0137695 A1 | 6/2005 | Salahieh et al. | |
| 2005/0137697 A1 | 6/2005 | Salahieh et al. | |
| 2005/0256566 A1 | 11/2005 | Gabbay | |
| 2005/0288251 A1 * | 12/2005 | Hales | C08B 37/0075 514/56 |
| 2006/0008497 A1 | 1/2006 | Gabbay | |
| 2006/0058872 A1 | 3/2006 | Salahieh et al. | |
| 2006/0074484 A1 | 4/2006 | Huber | |
| 2006/0122692 A1 | 6/2006 | Gilad et al. | |
| 2006/0149360 A1 | 7/2006 | Schwammenthal et al. | |
| 2006/0173532 A1 | 8/2006 | Flagle et al. | |
| 2006/0178740 A1 | 8/2006 | Stacchino et al. | |
| 2006/0206202 A1 | 9/2006 | Bonhoeffer et al. | |
| 2006/0241744 A1 | 10/2006 | Beith | |
| 2006/0241745 A1 | 10/2006 | Solem | |
| 2006/0259120 A1 | 11/2006 | Vongphakdy et al. | |
| 2006/0259137 A1 | 11/2006 | Artof et al. | |
| 2006/0265056 A1 | 11/2006 | Nguyen et al. | |
| 2006/0276813 A1 | 12/2006 | Greenberg | |
| 2006/0282157 A1 | 12/2006 | Hill et al. | |
| 2007/0010876 A1 | 1/2007 | Salahieh et al. | |
| 2007/0027534 A1 | 2/2007 | Bergheim et al. | |
| 2007/0043435 A1 | 2/2007 | Seguin et al. | |
| 2007/0055358 A1 | 3/2007 | Krolik et al. | |
| 2007/0067029 A1 | 3/2007 | Gabbay | |
| 2007/0093890 A1 | 4/2007 | Eliasen et al. | |
| 2007/0100435 A1 | 5/2007 | Case et al. | |
| 2007/0118210 A1 | 5/2007 | Pinchuk | |
| 2007/0213813 A1 | 9/2007 | Von Segesser et al. | |
| 2007/0233228 A1 | 10/2007 | Eberhardt et al. | |
| 2007/0244545 A1 | 10/2007 | Birdsall et al. | |
| 2007/0244552 A1 | 10/2007 | Salahieh et al. | |
| 2007/0288087 A1 | 12/2007 | Fearnot et al. | |
| 2008/0021552 A1 | 1/2008 | Gabbay | |
| 2008/0039934 A1 | 2/2008 | Styrc | |
| 2008/0071369 A1 | 3/2008 | Tuval et al. | |
| 2008/0082164 A1 | 4/2008 | Friedman | |
| 2008/0097595 A1 | 4/2008 | Gabbay | |
| 2008/0114452 A1 | 5/2008 | Gabbay | |
| 2008/0125853 A1 | 5/2008 | Bailey et al. | |
| 2008/0140189 A1 | 6/2008 | Nguyen et al. | |
| 2008/0147183 A1 | 6/2008 | Styrc | |
| 2008/0154355 A1 | 6/2008 | Benichou et al. | |
| 2008/0154356 A1 | 6/2008 | Obermiller et al. | |
| 2008/0243245 A1 | 10/2008 | Thambar et al. | |
| 2008/0255662 A1 | 10/2008 | Stacchino et al. | |
| 2008/0262602 A1 | 10/2008 | Wilk et al. | |
| 2008/0269879 A1 | 10/2008 | Sathe et al. | |
| 2009/0112309 A1 | 4/2009 | Jaramillo et al. | |
| 2009/0138079 A1 | 5/2009 | Tuval et al. | |
| 2010/0004740 A1 | 1/2010 | Seguin et al. | |
| 2010/0036484 A1 | 2/2010 | Hariton et al. | |
| 2010/0049306 A1 | 2/2010 | House et al. | |
| 2010/0082094 A1 | 4/2010 | Quadri et al. | |
| 2010/0087907 A1 | 4/2010 | Lattouf | |
| 2010/0131055 A1 | 5/2010 | Case et al. | |
| 2010/0168778 A1 | 7/2010 | Braido | |
| 2010/0168839 A1 | 7/2010 | Braido et al. | |
| 2010/0185277 A1 | 7/2010 | Braido et al. | |
| 2010/0191320 A1 | 7/2010 | Straubinger et al. | |
| 2010/0191326 A1 | 7/2010 | Alkhatib | |
| 2010/0204781 A1 | 8/2010 | Alkhatib | |
| 2010/0204785 A1 | 8/2010 | Alkhatib | |
| 2010/0217382 A1 | 8/2010 | Chau et al. | |
| 2010/0249911 A1 | 9/2010 | Alkhatib | |
| 2010/0249923 A1 | 9/2010 | Alkhatib et al. | |
| 2010/0262231 A1 | 10/2010 | Tuval et al. | |
| 2010/0286768 A1 | 11/2010 | Alkhatib | |
| 2010/0298931 A1 | 11/2010 | Quadri et al. | |
| 2010/0331972 A1 | 12/2010 | Pintor et al. | |
| 2011/0029072 A1 | 2/2011 | Gabbay | |
| 2011/0257739 A1 * | 10/2011 | Corbett | A61F 2/2412 623/2.18 |

(56) References Cited

U.S. PATENT DOCUMENTS

2013/0282113 A1  10/2013  Punga et al.
2013/0316087 A1* 11/2013  Ahn .................. B05D 7/52
                                            427/487

FOREIGN PATENT DOCUMENTS

| DE | 202008009610 U1 | 12/2008 |
|---|---|---|
| EP | 0850607 A1 | 7/1998 |
| EP | 1000590 A1 | 5/2000 |
| EP | 1360942 B1 | 11/2003 |
| EP | 1584306 A1 | 10/2005 |
| EP | 1598031 A2 | 11/2005 |
| EP | 1926455 A2 | 6/2008 |
| FR | 2847800 A1 | 6/2004 |
| FR | 2850008 A1 | 7/2004 |
| WO | 9117720 A1 | 11/1991 |
| WO | 9716133 A1 | 5/1997 |
| WO | 9832412 A2 | 7/1998 |
| WO | 9913801 A1 | 3/1999 |
| WO | 0128459 A1 | 4/2001 |
| WO | 0149213 A2 | 7/2001 |
| WO | 0154625 A1 | 8/2001 |
| WO | 0156500 A2 | 8/2001 |
| WO | 0176510 A2 | 10/2001 |
| WO | 0236048 A1 | 5/2002 |
| WO | 0247575 A2 | 6/2002 |
| WO | 03047468 A1 | 6/2003 |
| WO | 06073626 A2 | 7/2006 |
| WO | 2007016251 A2 | 2/2007 |
| WO | 07071436 A2 | 6/2007 |
| WO | 08070797 A2 | 6/2008 |
| WO | 2009106545 A1 | 9/2009 |
| WO | 2010008548 A2 | 1/2010 |
| WO | 2010008549 A1 | 1/2010 |
| WO | 2010096176 A1 | 8/2010 |
| WO | 2010098857 A1 | 9/2010 |

OTHER PUBLICATIONS

Li et al., U.S. Appl. No. 13/237,237, filed Sep. 20, 2011.
International Search Report and Written Opinion for Application No. PCT/US2013/048199 dated Dec. 4, 2013.
Quaden, R. et al., "Percutaneous aortic valve replacement: resection before implantation," European J. of Cardio-thoracic Surgery, May 2005, pp. 836-840, vol. 27, No. 5.
Ruiz, C., "Overview of PRE-CE Mark Transcatheter Aortic Valve Technologies," Euro PCR, May 2010 (Powerpoint dated May 25, 2010).
Knudsen, L. L. et al., Catheter-implanted prosthetic heart valves, The International Journal of Arlificial Organs, vol. 16, No. 5 1993, pp. 253-262.
Moazami, Nader, et al., Transluminal Aortic Valve Placement, ASAIO Journal, 1996; 42:M381-M385.
Andersen, Henning Rud, Transluminal Catheter Implanted Prosthetic Heart Valves, International Journal of Angiology 7:102-106 (1998).
Andersen, H.R., et al., Transluminal implantation of artificial heart valves, European Heart Journal (1992) 13, 704-708.
Zegdi, Rachid, MD, PhD. et al., Is It Reasonable to Treat All Calcified Stenotic Aortic Valves With a Valved Stent?, 579-584, J. of the American College of Cardiology, vol. 51, No. 5, Feb. 5, 2008.
U.S. Appl. No. 29/375,243, filed Sep. 20, 2010.

\* cited by examiner

STENT AND IMPLANTABLE VALVE INCORPORATING SAME

CROSS REFERENCE TO RELATED APPLICATION

The present application is a divisional of U.S. patent application Ser. No. 13/796,350 filed Mar. 12, 2013, and claims the benefit of the filing date of U.S. Provisional Patent Application No. 61/667,487 filed Jul. 3, 2012, the disclosures of which are hereby incorporated herein by reference.

BACKGROUND OF THE INVENTION

The present invention relates to implantable prosthetic valves and stents for use therein.

A prosthetic valve for use in replacing a natural valve of the cardiovascular system may incorporate a stent that acts as a supporting structure and a plurality of leaflets typically formed from a thin flexible material. The leaflets function in a manner similar to the leaflets of a natural valve so as to allow blood to flow in one direction but block blood flow in the opposite direction. For example, such a valve may be implanted at or near the site of the natural aortic valve to replace a defective aortic valve. The leaflets open during systole to allow flow in the distal direction from the left ventricle of the heart into the aorta, but close during diastole to block reverse blood flow in the proximal direction from the aorta into the heart.

Historically, prosthetic aortic valves have been implanted in an open-chest surgical procedure. More recently, valves suitable for implantation using a catheterization technique have been proposed. Such valves typically incorporate a stent generally in the form of an elongated. The valve leaflets are mounted to the stent. Typically, a covering of a flexible material commonly referred to as a cuff overlies a portion of the stent. The entire assembly, including the stent, leaflets, and cuff, is collapsible in radial directions relative to the axis of the stent. When the assembly is in a fully collapsed condition, the assembly is small enough in diameter to be carried on a catheter through the vascular system to the site of implantation. For example, a catheter may be inserted into an access site, such as the femoral artery, and advanced through the descending aorta, around the aortic arch, and into the ascending aorta to the site of the native aortic valve. At the implantation site, the stent is expanded to an expanded condition in which the stent grips the surrounding tissue and secures the assembly in place. In the expanded condition, the valve flaps are free to open and close to provide an action similar to that of the native valve. Expansion of the stent may be driven by an expansion device such as a balloon carried on the catheter inside the stent. In other cases, the stent is a self-expanding structure, typically formed from a metallic material such as a nickel-iron memory alloy commonly referred to as "nitinol" or other metallic alloy. Expandable stents of this type typically are formed as a mesh-like structure incorporating numerous elongated members joined at their ends with one another, so as to define cells of the mesh. For example, the members may be formed integrally with one another by etching or cutting a thin tube of the stent material so as to leave the mesh-like structure.

Collapsible and expandable valves of this nature most commonly are made with the flaps formed from a biologically derived material as, for example, bovine or porcine pericardial tissue. The cuffs typically are made from natural tissues or from synthetic material such a Dacron™ polyester fabric. It has also been proposed to form the valve leaflets from synthetic polymeric materials such as polyurethane compositions. U.S. Pat. Nos. 6,953,332 and 7,682,389, the disclosures of which are incorporated by reference herein, disclose certain valves having leaflets formed from synthetic polymers. Co-pending, commonly assigned U.S. Provisional Patent Application No. 61/512,999, filed Jul. 29, 2011, the disclosure of which is also incorporated by reference herein, discloses improvements in processes for forming valve leaflets by a dip-molding process, as well as an improved mandrel for use in such processes.

The leaflets of a prosthetic valve are subjected to significant stresses. Typically, each leaflet is a thin sheet having a curved free edge and another curved edge attached to the stent. The leaflets come together with one another at points referred to as commissures positioned at the ends of the attached edge. When the valve is in a closed condition, the free edges of the leaflets are bowed into the center of the stent so that the leaflets abut one another along their free edges or "coapt" with one another, so as to form a closed surface spanning the interior of the stent. When the leaflets are in the open position, the free edges of the leaflets are displaced outwardly towards the periphery of the stent, so that the free edges of the leaflets cooperatively define an opening for flow of the fluid. In the closed condition, the pressure of the blood distal from the valve is greater than the pressure of the blood proximal from the valve. In this condition, the pressure distal to the valve tends to pull the attached edges of the leaflets away from the stent and thus puts stress on the attachments between the attached edges and the stent. This stress is applied repeatedly, with every beat of the heart. As a replacement valve typically is expected to last for many years, it must withstand many billions of cycles of such stress.

Valve flaps formed from natural tissues typically are sutured to the stent. For example, as disclosed in co-pending, commonly assigned U.S. patent application Ser. No. 13/237,237, the disclosure of which is incorporated by reference herein, the attached edges of the stent may extend along some of the elongated members of the stent and may be sutured to such members.

Despite considerable attention devoted in the art heretofore to development of implantable valves and stents for the same, still improvement would be desirable. In particular, it would be desirable to provide a valve with improved attachment between the flaps and the stent, and to provide a stent having attachment features particularly suitable for forming such secure attachment. It would also be desirable to provide a valve incorporating a stent with such improved attachment. Such improvements would be desirable in all valves, and would be particularly desirable in the case of valves having leaflets formed from synthetic polymeric materials.

BRIEF SUMMARY OF THE INVENTION

One aspect of the invention provides a stent for an implantable valve. A stent according to this aspect of the invention desirably includes a proximal section extending circumferentially around an axis. The proximal section desirably includes a plurality of elongated proximal members connected with one another. Each of the proximal members has a mean perimeter. As referred to herein, the "perimeter" of an elongated member is the length of the path extending around the member in a plane perpendicular to the direction of elongation of the member. The stent according to this aspect of the invention desirably also includes a leaflet support section extending circumferentially around the axis. The leaflet support section is offset from the proximal section in a distal direction along the axis. The leaflet support section desirably includes a plurality of elongated leaflet support members which define a plurality of cusps or peaks projecting in the distal direction at locations spaced circumferentially around the axis. The leaflet support members desirably also define a plurality of recesses or valleys between the cusps, such that two of the leaflet support members bound each valley. The leaflet support members bounding the valleys desirably have mean perimeters that are greater than the mean perimeters of the proximal members. For example, the leaflet support members may be substantially wider than the proximal members. The stent as a whole desirably is collapsible and expandable in radial directions relative to the axis. As further discussed below, the relatively large dimensions of the leaflet support members help to distribute the stress in the attachment between the leaflets and the leaflet support members, and thus help to provide a secure attachment. The leaflet support members may have openings extending through these members in the thickness direction of the members, i.e., the direction that faces in a generally radial direction in the expanded condition of the stent.

A further aspect of the invention provides an implantable valve that includes a stent as discussed above and a plurality of leaflets mounted to the stent. Each such leaflet spans one of the valleys and has an attached edge secured to and extending along the leaflet support members bounding the valley. Each such leaflet has a free edge extending between the cusps which are disposed on opposite sides of the valley, so that the free edges of the leaflets meet one another at commissures adjacent the cusps of the stent. In certain embodiments, the leaflets may be formed form a polymeric material. The leaflets may adhere to the leaflet support members. Where the leaflet support members have openings extending into them, the synthetic polymeric material integral with the leaflets may extend into the openings so as to help secure the leaflets to the leaflet support members.

Still further aspects of the invention provide methods of making an implantable valve. One method according to this aspect of the invention includes the steps of placing a mandrel having leaflet-forming surfaces within a stent having spaced-apart elongated leaflet support members with openings therein so that the leaflet support members of the stent extend along edges of the leaflet-forming surface of the mandrel, and the leaflet-forming surfaces of the mandrel span between the leaflet-supporting members. The method according to this aspect of the invention desirably also includes the step of depositing a flowable composition on the mandrel and the stent so that the composition forms layers on the leaflet-supporting surfaces spanning between the members of the stent, contacts the members of the stent, and penetrates into the openings of the members, and curing the composition to a flexible solid so as to form leaflets as films extending between the leaflet-supporting members, the leaflets being secured to the members at least in part by cured composition in the openings, and removing the stent and films from the mandrel.

BRIEF DESCRIPTION OF THE DRAWINGS

These and other objects, features, and advantages of the present invention will be more readily apparent from the detailed description set forth below, taken in conjunction with the accompanying drawings, in which.

DETAILED DESCRIPTION

A stent 20 in accordance with one embodiment of the invention (FIGS. 1 and 2) incorporates a proximal section 22 extending in circumferential directions C (FIG. 2) around a proximal-to-distal axis 24. The proximal section incorporates a plurality of elongated proximal members 26, which are connected to one another so as to form the proximal section. In the particular embodiment shown, the proximal members 26 intersect one another at junctures 29 so as to define a plurality of closed proximal cells 28, each surrounded by proximal members. The particular structure depicted in FIGS. 1 and 2 incorporates two rows of such proximal cells, these rows being offset from one another in the proximal-to-distal directions along axis 24. In the expanded condition shown in FIGS. 1 and 2, the proximal section defines a bore coaxial with axis 24.

Figure 2:
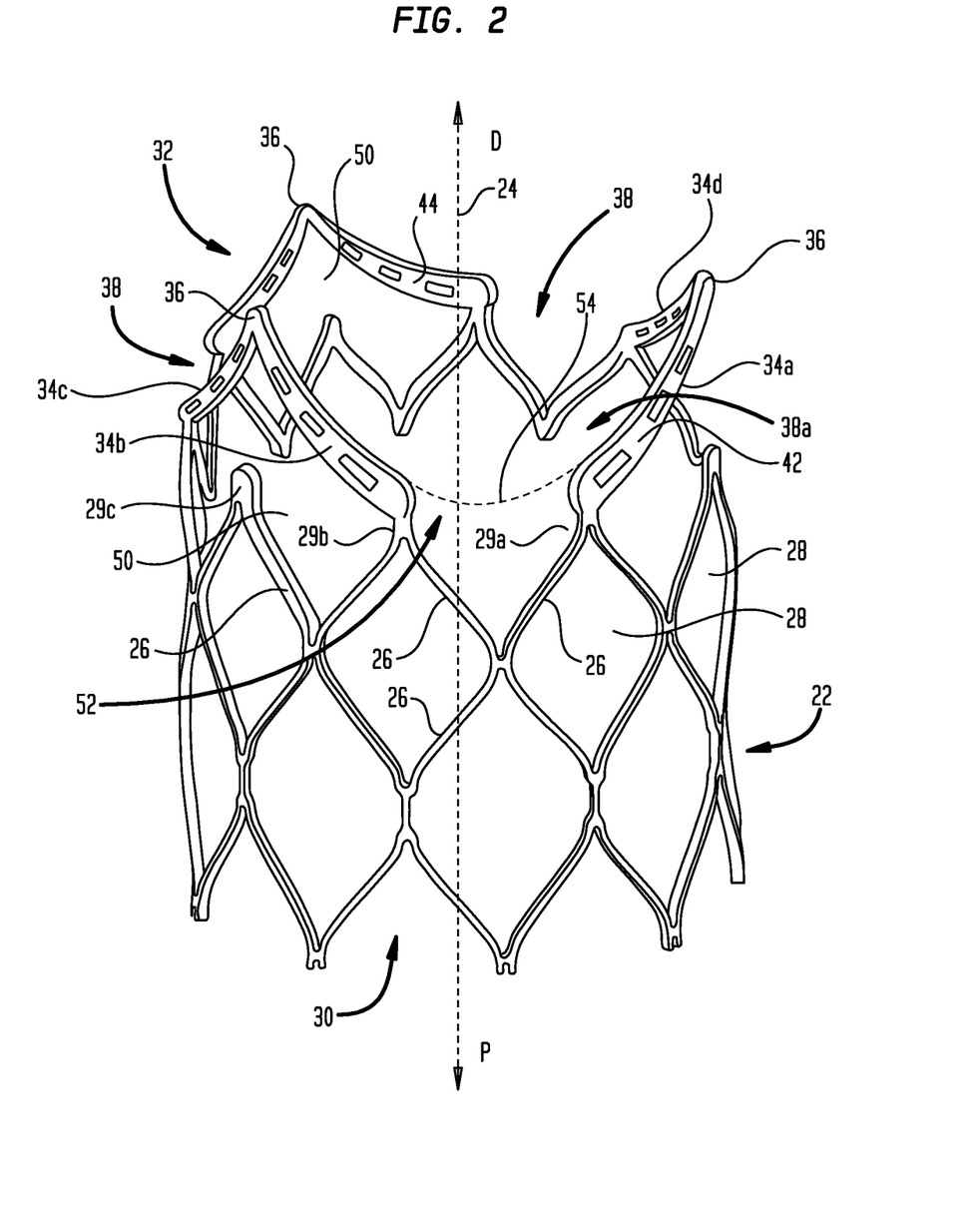
FIG. 2 is a diagrammatic perspective view depicting the stent of FIG. 1 with portions removed for clarity of illustration.
Figure 3:
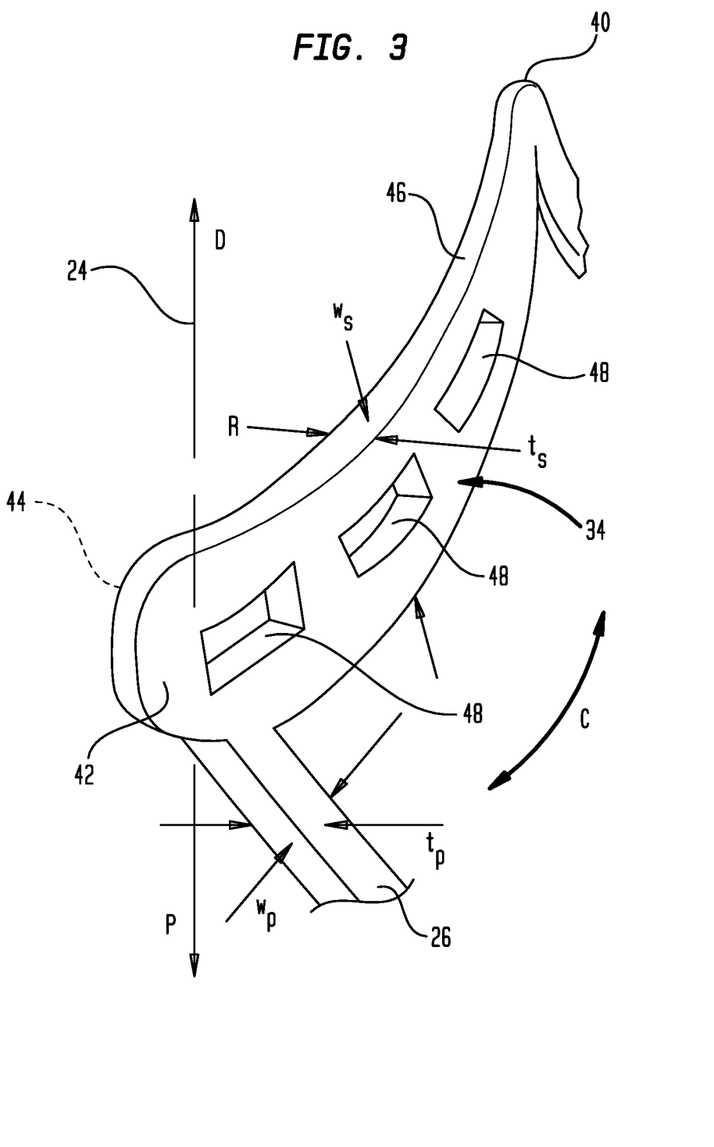
FIG. 3 is a diagrammatic perspective view of a member used in the stent of FIGS. 1 and 2.

The stent further includes a leaflet support section 32 offset from the proximal section 22 in the distal direction along axis 24. The leaflet support section includes a plurality of elongated leaflet support members 34. As best appreciated with reference to FIG. 2, each leaflet support member extends circumferentially around the axis and also extends in the axial or proximal-to-distal directions. The leaflet support members join one another at their distal ends, so as to define cusps or projections 36 projecting in the distal direction, away from the proximal section 22, and valleys or recesses 38 interspersed with the cusps. In the particular embodiment depicted, there are three cusps and three valleys. Two of the leaflet support members bound each valley. For example, leaflet support members 34a and 34b bound valley 38a on opposite sides thereof. Leaflet support members 34a and 34d join one another at distal ends to define one of the cusps 36, whereas leaflet support member 34b joins leaflet support member 34c so as to form another cusp 36 on the opposite side of valley 38a. The leaflet support members are generally curvilinear. Each leaflet support member is generally elongated, and the direction of elongation extends along a curving axis 40 (FIG. 3). As best appreciated with reference to FIG. 2, when the stent is in an expanded condition, the various members of the stent extend generally along a surface that is a surface of revolution about axis 24. The direction of elongation 40 of each member extends generally along this surface. Each leaflet support member has a width $W_S$ (FIG. 3) in a direction transverse to the direction of elongation 40. When the stent is in the expanded condition depicted, the width $W_S$ lies in a direction transverse to the radial direction from axis 24 to the member. As will be appreciated from FIGS. 1-3, the width $W_S$ of the leaflet support member varies along the length or direction of elongation 40 of the member. Each leaflet support member 34 also has a thickness $T_S$ transverse to the direction of elongation and transverse to the width $W_S$. In the expanded condition depicted, the thickness direction $T_S$ extends in the radial direction relative to axis 24. Stated another way, the thickness dimension $T_S$ lies along a radius extending outwardly from the axis to the member. The dimensions $T_s$ and $W_s$ are the dimensions of the member measured in a plane perpendicular to the direction of elongation of the member. In the embodiment depicted, the width dimension of the leaflet support member 34 varies along the direction of elongation, whereas the thickness $T_S$ remains constant. The mean width direction $W_S$ of the leaflet support member is substantially larger than the thickness $T_S$ of the same member. The mean width $W_S$ of each leaflet support member desirably is at least about 1.5 times, and preferably at least about 2 times, the mean thickness $T_S$ of each leaflet support member. Thus, the leaflet support member has major surfaces including an outer surface 42 facing generally outwardly, away from axis 24 in the expanded condition of the stent, and an inner surface 44 (best seen in FIG. 2) facing generally inwardly, toward the axis. These major surfaces 42 and 44 have relatively large surface area as compared to the lateral surfaces 46, which face generally in axial directions when the stent is in the expanded condition.

Each leaflet support member also has openings extending through the leaflet support between its outer surface 42 and its inner surface 44. Desirably, each leaflet support member has a plurality of such openings spaced along the direction of elongation 40 of the member. In the particular embodiment depicted, each opening 48 is in the form of an elongated slot extending in the direction of elongation of the member, although other openings such as circular bores can be employed.

As best appreciated with reference to FIG. 3, the mean width $W_S$ of the leaflet support members is greater than the mean width $W_P$ of the proximal members 26, whereas the thickness $T_S$ of the leaflet support members is substantially equal to the thickness $T_P$ of the proximal members 26. Here again, the width of an elongated member, such as member 26, is the dimension transverse to the direction of elongation of the member and lying generally along the surface of revolution defined by the stent. Stated another way, the width $W^P$ is the dimension transverse to the radial direction from axis 24 to the member when the stent is in the expanded condition. The thickness $T_P$ is the dimension of the member transverse to the direction of elongation of the member and also transverse to the width direction. Thus, the thickness $T_P$ is the dimension of member 26 in the radial direction R from the axis to the member when the stent is in the expanded condition. Desirably, the mean width of all of the leaflet support members 34 that bound the valleys of the leaflet support section is substantially greater than the mean width of all of proximal members 26 taken in the aggregate. Most preferably, each leaflet support member has a mean width that is greater than the mean width of any of the individual proximal members 26.

At any point along the length of a leaflet support member 34, the perimeter of the member measured in a plane perpendicular to the direction of elongation of 40 of the member is simply twice the thickness $T_S$ plus twice the width $W_S$. Likewise, the perimeter of proximal member 26 is twice the width $W_P$ plus twice the thickness $T_P$. Unless otherwise indicated, references to the "perimeter" of an elongated member refer to the perimeter of the member as measured in a plane perpendicular to the direction of elongation of the member. As will be appreciated from FIG. 3, mean perimeter each leaflet support member 34 is greater than the mean perimeter of proximal member 26. Desirably, the mean perimeter of all leaflet support members in the aggregate is greater than the mean perimeter of all of the proximal members 26 in the aggregate, and more desirably each leaflet support member has a mean perimeter greater than the mean perimeter of any individual proximal member 26.

Figure 1:
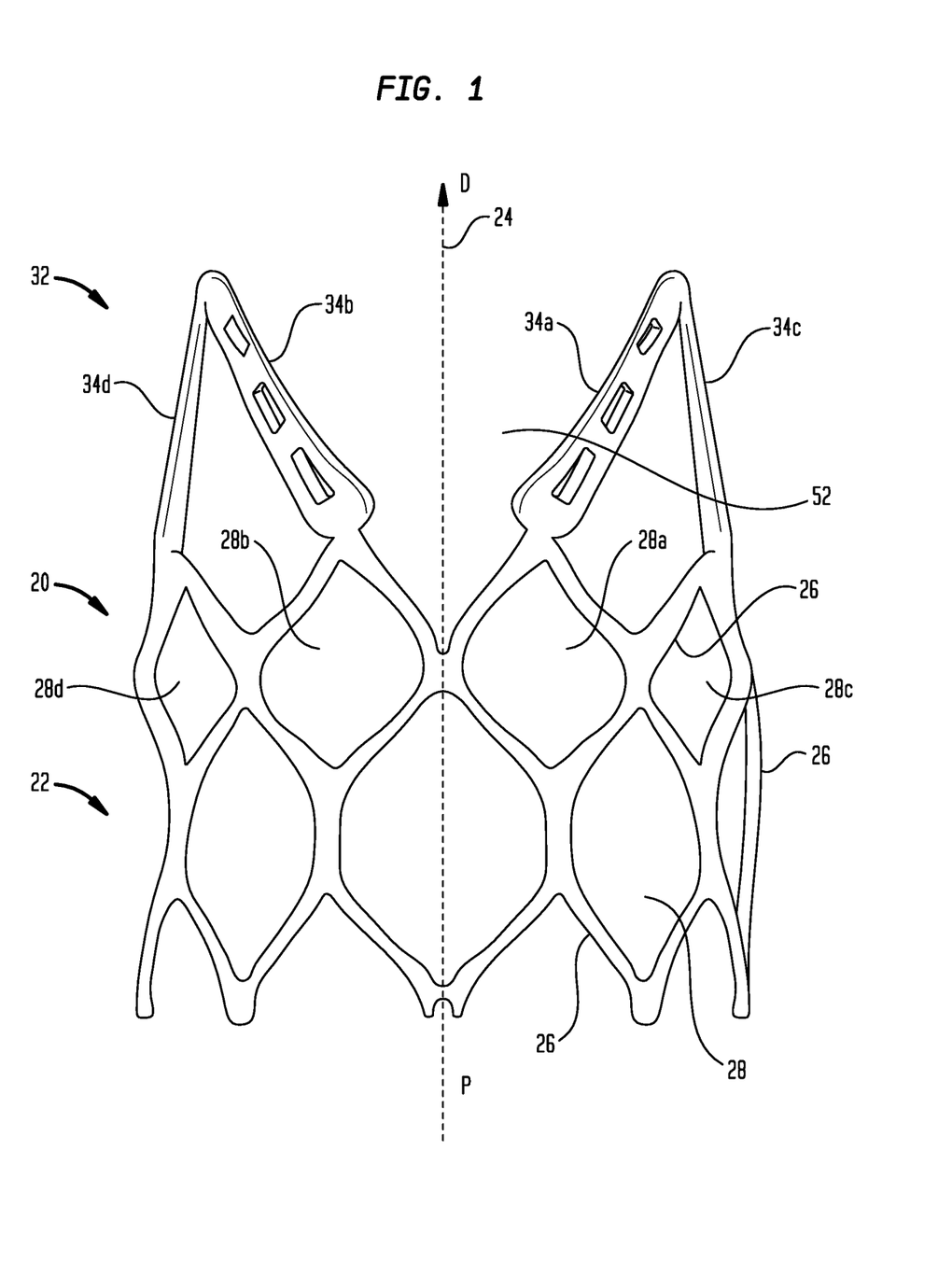
FIG. 1 is a diagrammatic elevational view of a stent according to one embodiment of the invention.

The proximal ends of leaflet support members 34 join some of the distal-most junctures 29 of the proximal section. The leaflet support members bounding each valley 38 are joined to mutually adjacent junctures 29. For example, the proximal ends of leaflet support members 34a and 34b bounding valley 38a join junctures 29a and 29b (FIG. 2). Thus, the proximal ends of the leaflet support members bounding each valley 38 are spaced apart from one another in the circumferential direction so as to leave a gap 52 between them. This gap extends across the distance between the mutually adjacent intersection junctures 29a and 29b of the proximal section. As also seen in FIGS. 1 and 2, the leaflet support members bounding each gap define sections of a continuous curve 54 depicted in broken lines in FIG. 2. Such continuous curve extends from the cusps 36 adjacent to the valley 38, and extends across the gap 52 defined between the proximal ends of the leaflet support members. Curve 54 may be generally in the form of a parabola, catenary, arc, or other continuous curve.

The two leaflet support members defining a cusp 36 span across one juncture 29. For example, leaflet support members 34b and 34c span across juncture point 29c. Thus, the leaflet support members 34, and some of the members of the proximal sections, define relatively large, closed cells 50. The entire stent, including the proximal section and the leaflet support section, desirably is collapsible from the expanded condition depicted to a compressed condition in which the radial dimensions of the stent are substantially reduced, and expandable from such collapsed condition back to the expanded condition.

Figure 4:
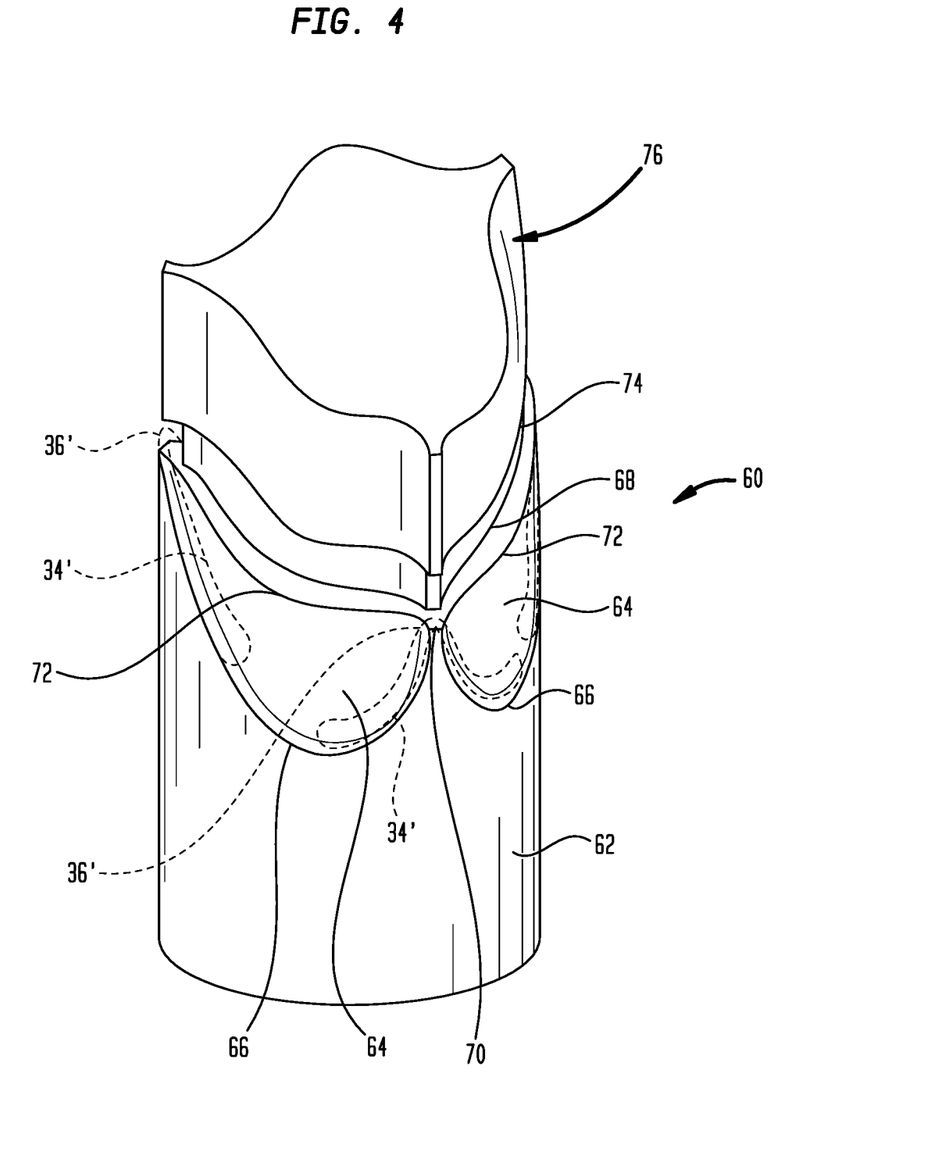
FIG. 4 is a diagrammatic perspective view depicting a mandrel utilized in accordance with a leaflet-forming process.

A mandrel 60 (FIG. 4) used in a valve fabrication process includes a generally cylindrical main surface 62 and three leaflet-forming surfaces 64, of which only two are visible in FIG. 4. Each leaflet-forming surface 64 is recessed slightly relative to the main surface 62, so that there is a ledge 66 at the juncture of the leaflet-forming surface with the main surface. Each ledge 66 forms a boundary of the associated leaflet-forming surface 64. The ledges 66 are generally curvilinear and are concave in a forward direction, toward the top of the drawing in FIG. 4. The ledges 66 approach one another, but do not intersect one another, adjacent convergence points 70. The main surface 62 extends upwardly between adjacent ledges 66 to each convergence point 70. A step 68 extends inwardly, toward the central axis of the mandrel from leaflet-forming surfaces 64 and from the convergence points 70. The step defines a free edge 72 for each leaflet-forming surface. A neck portion 74 having dimensions smaller than the free edges of the leaflet-forming surfaces projects in the forward direction from step 70. A forward portion 76 of the mandrel is disposed at the end of neck portion 74 remote from step 68 and the leaflet-forming surfaces. This forward portion 76 has a cross-sectional shape similar to that of the leaflet-forming surfaces 66, and has dimensions similar to those of the leaflet-forming surfaces. This mandrel may be in accordance with the disclosure of the aforementioned U.S. Provisional Patent Application No. 61/512,999.

In a manufacturing process according to one embodiment of the invention, mandrel 60 is positioned inside stent 20 (FIGS. 1-3) while the stent is in the expanded condition depicted in FIGS. 1 and 2. The main surface 62 lies within the proximal section 22 of the stent, whereas the leaflet-forming surfaces 64 are positioned inside or near the leaflet support section 32 in alignment with valleys 38, so that the leaflet support elements 34 of the stent (FIGS. 1 and 2) extend generally near the edges of the leaflet-forming surfaces 64 defined by ledges 66. This is depicted schematically in FIG. 4, where the positions of the leaflet support elements 34 are depicted in broken lines at 34'. The cusps 36 defined by the leaflet-supporting elements lie adjacent the convergence points 70 of the mandrel, as indicated in broken lines at 36' in FIG. 4.

While the stent and mandrel are in this assembled condition, they are dipped into a flowable composition, which can be cured to a solid condition. The flowable composition may be, for example, a solution of one or more polymers in a solvent that can be cured by driving off the solvents; a plastisol comprised of polymer materials in a liquid miscible with the polymer so that the composition can be cured by absorption of the solvent into the polymer; or a mixture containing chemically-reactive moieties that can be cured to a solid form by the reaction between the moieties. The polymer, when cured, desirably is non-toxic, non-carcinogenic, and does not induce substantial hemolysis or a substantial immunological response, so that the resulting prosthesis is substantially non-thrombogenic. The preferred polymers exhibit combinations of stiffness, strength, creep resistance, hardness, fatigue resistance, and tear resistance so as to form a durable valve that can last for years when implanted.

Suitable polymeric materials for formation into the leaflets include, for example, synthetic polymers as well as purified biological polymers and combinations thereof. Flexible polymers include elastomers and other polymers that can sustain significant flexure, bending, twisting, wear and/or deformation without structural failure. Appropriate synthetic polymers include, without limitation, polyamides (e.g., nylon), polyesters, polyacrylates, vinyl polymers (e.g., polyolefins, polyethylene, polytetrafluoroethylene or other halogenated polymers, polypropylene, ethylene-propylene copolymers, ethylene-propylene-diene monomer copolymer (EPDM) and polyvinylchloride), polycarbonates, polyacetals (e.g., Delrin®), polyurethanes, polyurethane-silicone copolymers, poly(styrene-b-isobutylene-b-styrene), polydimethyl siloxanes, cellulose acetates, ethylene vinyl acetates, polysulfones, nitrocelluloses, derivatives thereof, similar copolymers, and mixtures thereof. Particularly preferred flexible polymer materials for the formation of flexible polymer heart valve leaflets include, for example, polyurethanes, polyurethane-silicone copolymers, poly(styrene-b-isobutylene-b-styrene), polydimethyl siloxanes, polytetrafluoroethylenes, derivatives thereof and mixtures thereof.

Biological polymers can be naturally occurring or produced in vitro by, for example, fermentation and the like. Suitable biological polymers include, without limitation, collagen, elastin, silk, keratin, gelatin, polyamino acids, polysaccharides (e.g., cellulose and starch), and copolymers thereof.

Figure 5:
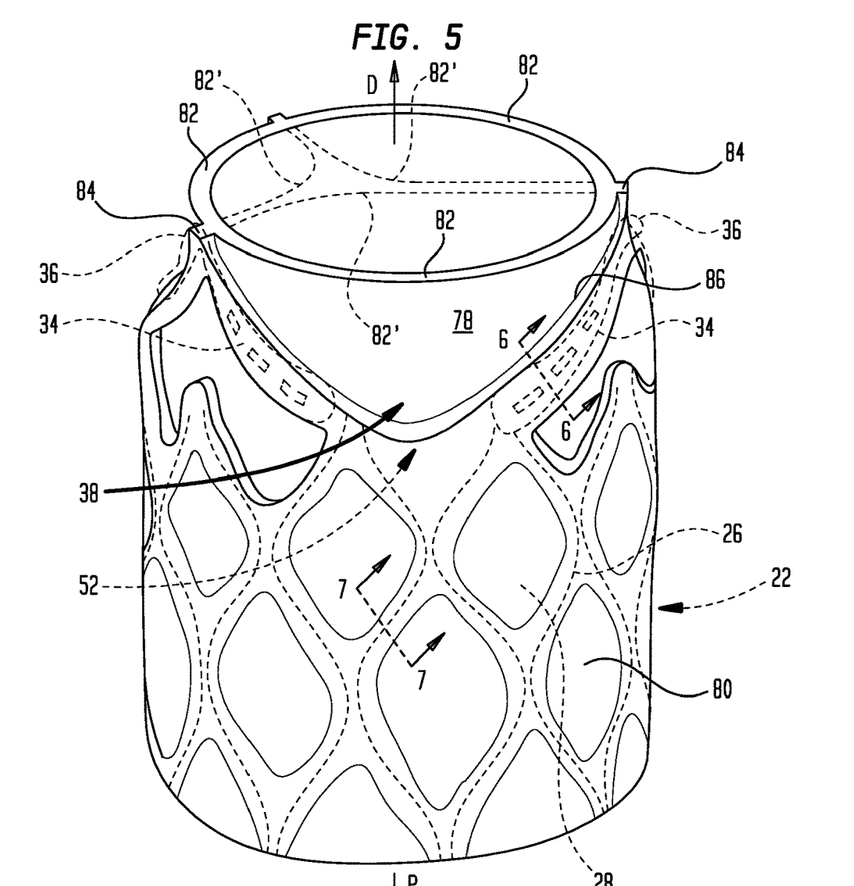
FIG. 5 is a diagrammatic perspective view depicting a valve incorporating the stent of FIGS. 1-3.

When the mandrel and stent are withdrawn from the dipping material, a film of dipping material clings to the mandrel and the stent. The film is then cured and trimmed off along the free edges 72 of the leaflet-forming surfaces at step 68. The resulting structure includes leaflets 78 and a cuff 80 depicted in FIGS. 5, 6, and 7. Each leaflet 78 extends across one valley 38 defined between a pair of leaflet support members 34. Each leaflet has a free edge 82 that extends between the cusps 36 disposed on opposite sides of the valley. The free edges 82 of adjacent leaves join one another at commissures 84 disposed at or adjacent the cusps 36. Each leaflet 78 also has an attached edge 86 extending generally along the leaflet support members 34 bounding the valley 38 associated with the leaflet. The attached edge 86 of the leaflet defines a curve corresponding to the curve 54 (FIG. 2) defined by the adjacent leaflet support members. The curvilinear path is generally concave in the downstream or distal direction D. A portion of the attached edge 86 extends across the gap 52 between the proximal ends of the adjacent support members 34. Leaflets 78 desirably are relatively thin and flexible. For example, the leaflets may have a thickness of about 50 microns to about 1,000 microns, and more preferably from about 100 microns to about 300 microns.

Figure 6:
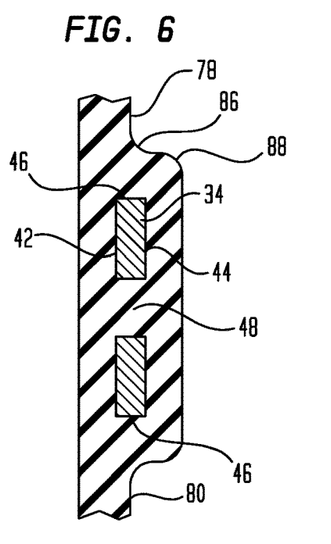
FIG. 6 is a diagrammatic sectional view on an enlarged scale taken along lines 6-6 in FIG. 5.
Figure 7:
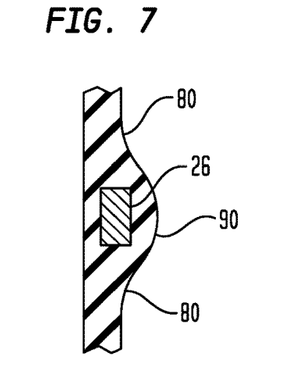
FIG. 7 is a diagrammatic sectional view on an enlarged scale taken along lines 7-7 in FIG. 5.

As best appreciated with reference to FIG. 6, polymer integral with each leaflet 78 surrounds the adjacent leaflet support members 34 so as to form attachments 88 integral with the leaflet 78 and extending adjacent the attached edge 86 thereof. The attachment 88 overlies the inner surface 42 and outer surface 44 of the leaflet support member and also extends over the edge surfaces 46 of the leaflet support member. Further, the polymer of the attachment 88 extends into and through the openings 48 of the leaflet support member. The large area of contact between the surfaces 42, 44, and 46 and the polymer provides a secure bond between the attachment and the leaflet support member, which is further reinforced by the mechanical interlocking of the polymer and the support member provided by the polymer within the openings 48. Thus, the attachments 88 provide a very secure connection between of the attached edge of each leaflet and the stent. This secure attachment extends all the way from the cusps 36 to the proximal ends of leaflet support members 34 at gap 52. A portion of the attached edge 86 extending across the gap 52 is left unsecured. However, this portion is exposed to relatively low stresses in service, and therefore the absence of support in this region is acceptable.

Cuff 80 is generally tubular and extends from the proximal end of the proximal section 22 of the stent to the leaflet support members and leaflets. Cuff 80 is a continuous film of polymeric material, which bridges across the proximal cells 28 and encompasses the proximal members 26, depicted schematically in broken lines in FIG. 5. As best appreciated with reference to FIG. 7, the polymer forms attachments 90 extending along each proximal member and surrounding the proximal member 26. These attachments 90 are integral with the cuff 80. Cuff 80 also spans across the larger cells 50 defined between the proximal members 26 and the leaflet support members 34. Thus, in the expanded condition shown, cuff 80 provides a substantially enclosed conduit leading from the proximal end of the stent to the leaflets 78.

In service, the valve is implanted in the cardiovascular system with the proximal section facing in the proximal or upstream direction and with the leaflets facing in the distal or downstream direction of the patient's circulatory system. The valve, including the stent, the cuff, and the flaps, is collapsed to a collapsed condition in which the diameter of the stent and valve are reduced. While the valve is in this condition, it is advanced to a position of implantation by catheterization techniques and expanded at the desired implantation site. For example, where the valve is used to replace the natural aortic valve, the valve typically is implanted at or near the annulus of the native aortic valve, so that the proximal section 22 of the stent and the cuff bear against the annulus of the native valve and anchor the valve in place. The blood flows in the distal direction from the left ventricle of the heart and out of the distal end of the implanted valve. During systole, the leaflets are in the open position shown in solid lines in FIG. 5. During diastole, the leaflets move to the closed position depicted in broken lines in FIG. 5. In this condition, the free edges 82 of the leaflets extend inwardly from commissures 84 towards the central axis of the stent and valve, so that the free edges 82 abut one another as depicted in broken lines at 82' and thus coapt with one another so as to block blood flow in the proximal or upstream direction. During this phase of operation, the leaflets are under significant stress from the systemic blood pressure, which tends to push the leaflets back in the proximal direction. Moreover, this stress is applied cyclically, every time the heart beats. A typical valve may endure 40 million stress cycles per year. The valve desirably should last for 20 to 30 years or more, and thus may endure on the order of $10^9$ cycles of cyclic stress. The cyclical stress on the leaflets is greatest on those portions of the leaflets adjacent the commissures 84 and thus adjacent the cusps 36 of the stent. The very secure attachments between the leaflets and the leaflet support members in these regions help the valve to resist the stresses applied to it in service. Further, this secure attachment is achieved using a relatively simple manufacturing process.

Figure 8:
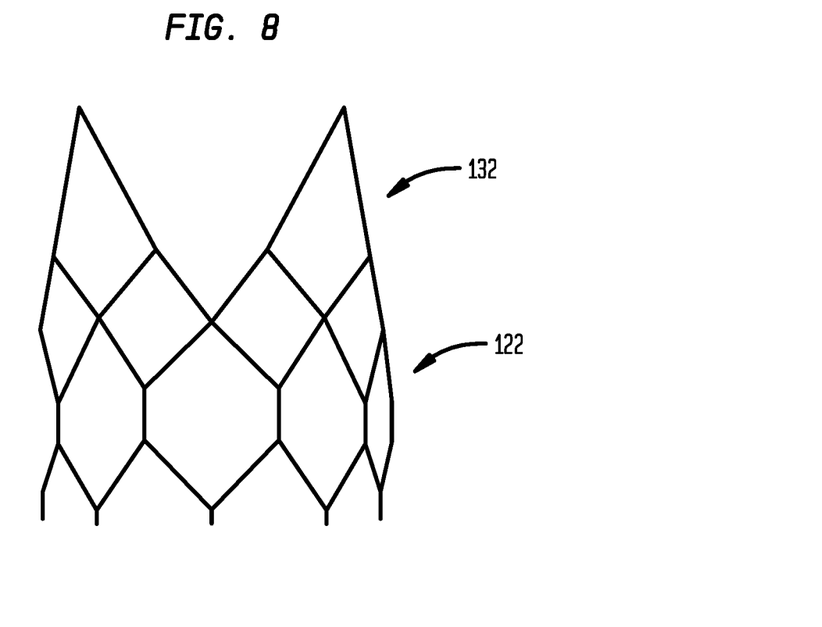
FIG. 8 is a diagrammatic elevational view of a stent according to a further embodiment of the invention.

Numerous variations of the features discussed above can be utilized without departing from the present invention. For example, the proximal section need not be cylindrical. For example, a stent schematically depicted in FIG. 8 has a proximal section 122 that flares outwardly, away from the central axis of the stent at its proximal end, and that also flares outwardly at the distal end of the proximal section, adjacent leaflet support section 132, so that the proximal section defines a relatively narrow portion between the proximal and distal ends of the proximal section. Such a configuration may be used, for example, to better secure the proximal section in engagement with the annulus of a native valve. In other embodiments, the proximal section of the stent may be tapered or barrel-shaped, and may be in the form of any surface of revolution about the central axis of the stent. In still other embodiments, the proximal section is not in the form of a surface of revolution. For example, where the valve is to be installed in the annulus of a native tricuspid valve such as the aortic valve, the native annulus and the native leaflets may define a generally triangular opening, and the proximal section of the stent may have a corresponding shape when in the expanded condition.

Figure 9:
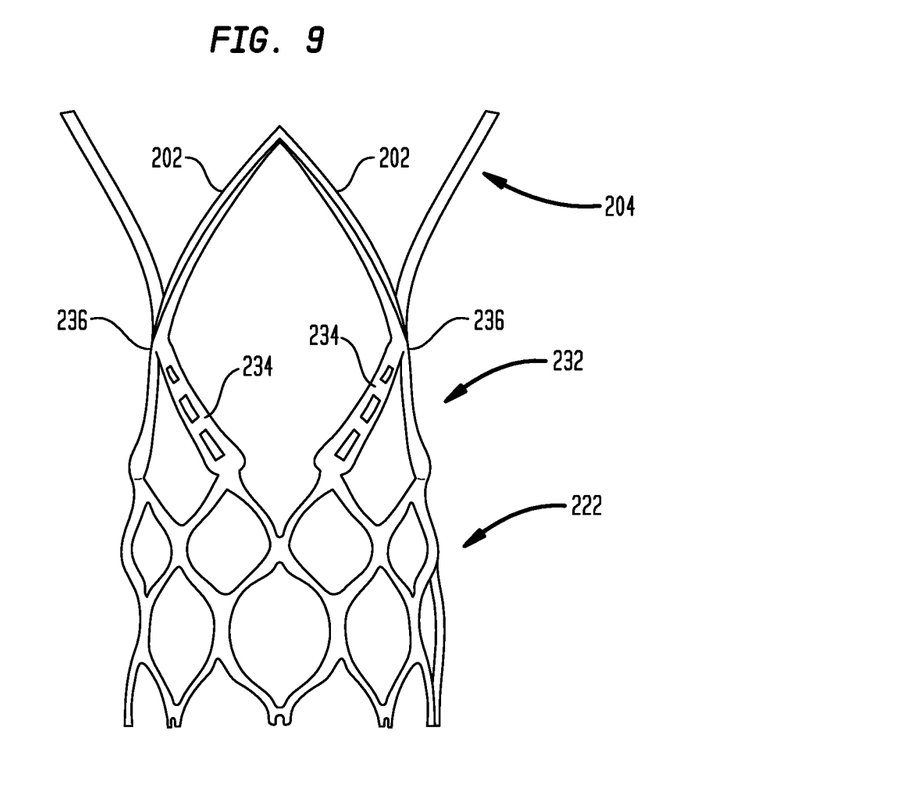
FIG. 9 is a diagrammatic elevational view of a stent according to yet another embodiment of the invention.

The stent of FIG. 9 is similar to the stent of FIGS. 1-5. However, the stent further includes a plurality of anchor members 202 defining an anchor section 204 distal to the leaflet support section 232. The anchor members 202 project generally distally from the cusps 236 defined by leaflet support members 234, so that the anchor members 202 and leaflet support members 234 define large cells. The leaflets are formed as discussed above with reference to FIGS. 5-7, so that the leaflets extend across the valleys defined between leaflet support members 234 and the free edges lie adjacent the cusps 236. Thus, the anchor members 202 extend downstream from the free edges of the leaflets. Those parts of the cells of anchor section 204 distal to the leaflets are open to allow flow of blood through the cells. A valve incorporating the stent of FIG. 9 may be implanted to replace an aortic valve. The proximal section 222 is disposed within the annulus of the native aortic valve, whereas and the anchor section 204 engages the aorta distal to the sinuses of Valsalva. Thus, blood can flow through the openings between the anchor members and reach the openings of the coronary arteries. Anchor section 204 helps to secure the valve in place.

Figure 10:
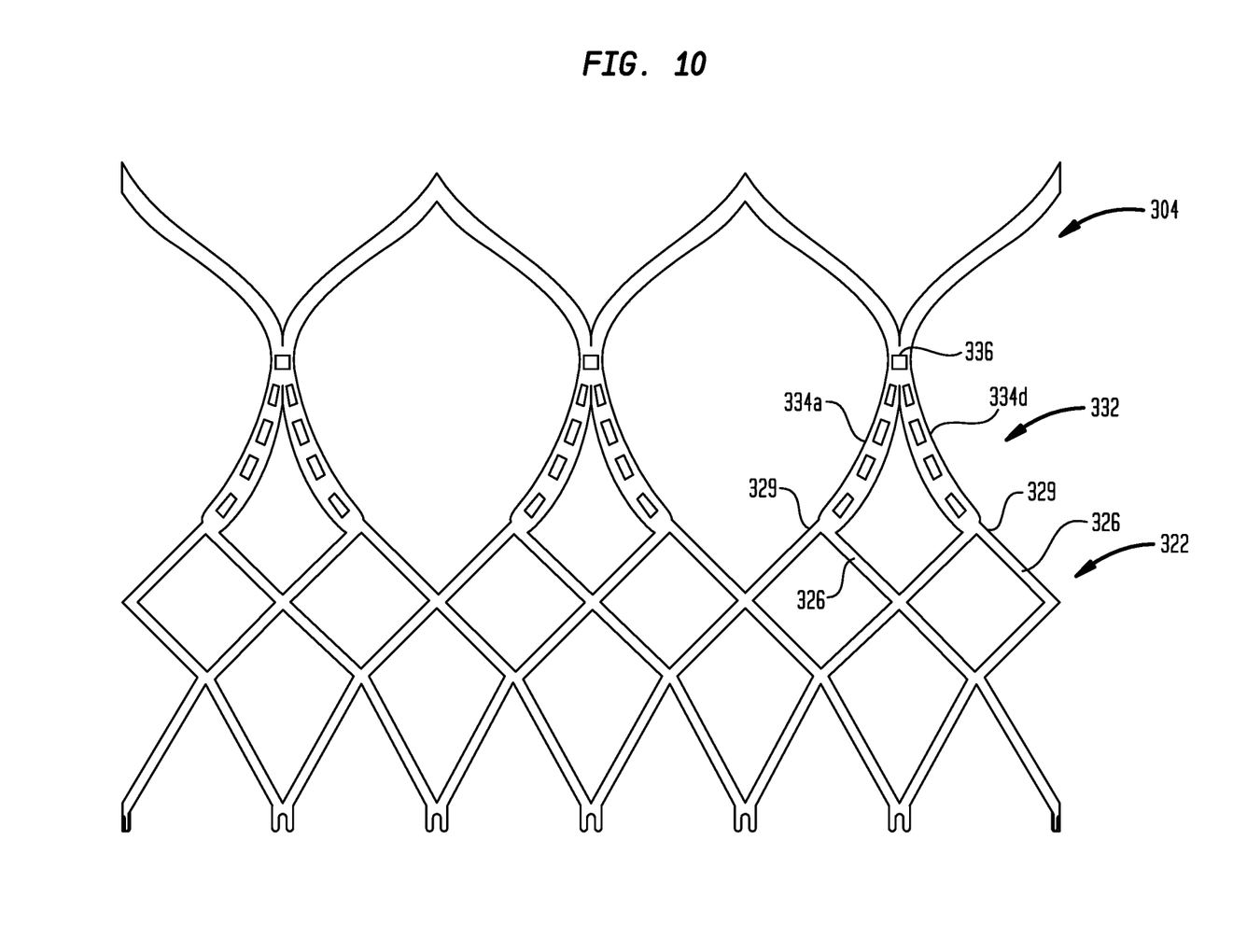
FIG. 10 is a diagrammatic view of a stent according to yet another embodiment, shown in a flat or unrolled condition for clarity of illustration.

A stent according to a further embodiment (FIG. 10) is depicted in planar view. Thus, the members of the stent are depicted in the positions they would have if the stent were cut along a single line parallel to the axis and unrolled to a flat structure. The stent according to the embodiment of FIG. 10 has a proximal section 322, leaflet-supporting section 332, and anchor section 304 generally similar to the corresponding structures in FIGS. 1-9. In this embodiment, however, the leaflet support members 334a and 334d, which cooperatively define a cusp 336, do not span across a juncture 329 of the proximal members 326. Rather, the two leaflet support members that define a cusp form a relatively small cell with the adjacent proximal members 326.

Figure 11:
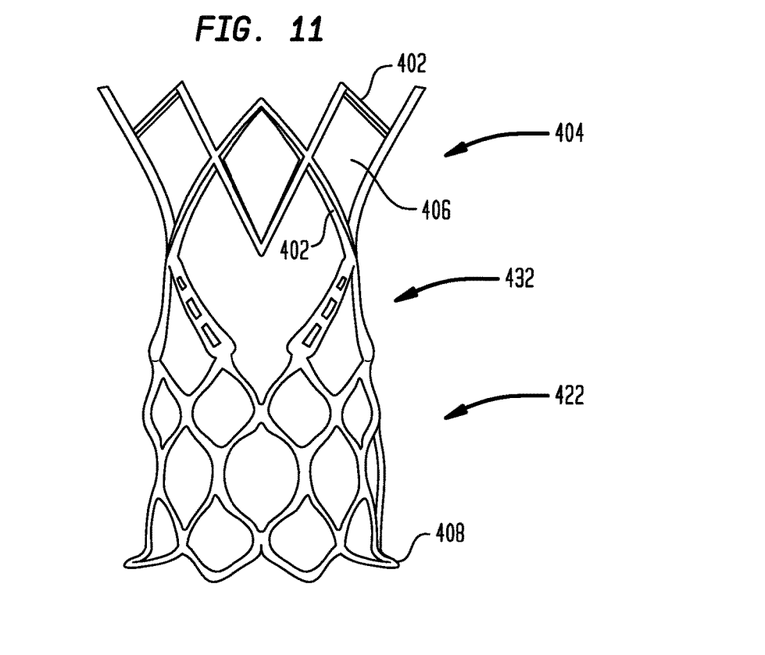
FIG. 11 is a diagrammatic elevational view depicting a stent according to yet another embodiment of the invention.

A stent according to yet another embodiment (FIG. 11) has a proximal section 422 and leaflet support section 432 similar to those discussed above, but has an anchor section 404 having more numerous anchor members 402, so that the anchor members cooperatively define an additional row of closed cells 406. Any number of such rows of cells can be provided in the anchor section. Also, the stent of FIG. 11 has an additional row of members 408 disposed at the proximal end of the proximal section 422. These members 408 cooperatively define an outwardly flaring anchor at the proximal end of the proximal section 422.

Figure 12:
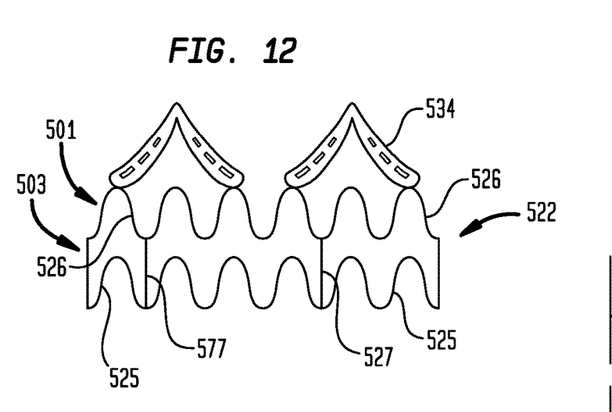
FIG. 12 is a diagrammatic elevational view depicting a stent according to yet another embodiment of the invention.

In a stent according to yet another embodiment (FIG. 12), the proximal members are not arranged in a grid of cells, as shown in the preceding figures. Rather, the proximal members include members 526, which join one another to form an undulating structure extending in a first ring 501 around the central axis of the stent. The proximal members further include members 525, which join one another to form a second, similar undulating ring 503 and longitudinal members 527, which extend between these two rings. Here again, the mean perimeter of the leaflet-supporting members 534 is greater than the mean perimeter of proximal members 525, 526, and 527 in the aggregate.

Figure 13:
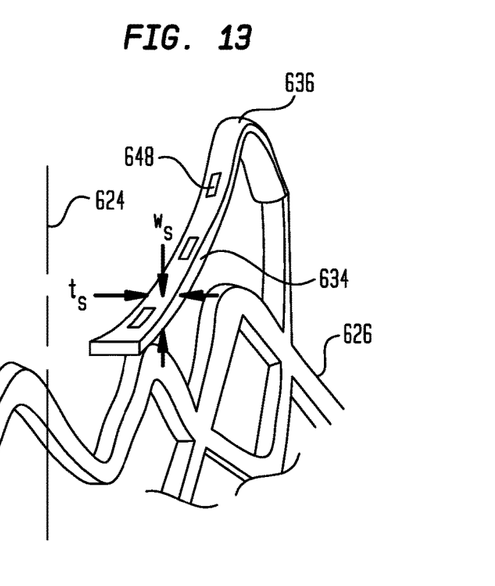
FIG. 13 is a fragmentary diagrammatic perspective view depicting a portion of a stent according to yet another embodiment of the invention.

In a stent according to a further embodiment of the invention, partially depicted in FIG. 13, each leaflet-supporting member 634 has a thickness or dimension in the radial direction relative to the central axis 624, which is substantially greater than the width of the member. Here again, the perimeter of the leaflet-supporting member desirably is greater than the perimeter of an individual proximal member 626, and the mean perimeter of the leaflet-supporting members as a whole desirably is greater than the mean perimeter of all of the proximal members 626. Here again, each leaflet-supporting member 634 has a pair of opposed major surfaces with relatively large area, and the openings 648 in the leaflet-supporting members extend between these major surfaces. A stent according to this embodiment of the invention may be made, for example, by bending or deforming the metal of a tubular member after etching to form the leaflet-supporting members. Alternatively, the leaflet-supporting members can be formed as separate strips, whereas the proximal section may be formed by etching a tubular member. The leaflet-supporting sections may then be attached to the proximal section as, for example, by welding the leaflet-supporting sections to the proximal member. If an anchor section is to be joined to the leaflet-supporting members, the anchor section may be welded to the cusps 636 of the leaflet-supporting members.

In a further variant, the leaflet-supporting members may be formed without openings, or with openings that extend only partially through the members. The relatively large surface areas of the leaflet-supporting members will still provide substantial securement between the polymer elements and the stent.

In the embodiments discussed above, the leaflets and cuff are formed by dip-molding while the mandrel is in place within the stent. Other processes can be used. For example, the leaflets can be prepared separately and then bonded to the stent as, for example, by applying a flowable mass of the polymer and curing the same, so as to form an attachment between the leaflets and the leaflet support members similar to that discussed above. In other versions, the leaflets may be glued to the surfaces to the leaflet support members. The cuff may be attached in a similar fashion. In still further variants, the leaflets may be sutured to the leaflet-supporting members. Such suturing may be used in addition to, or in lieu of, attachments as discussed above. The valves discussed above utilize polymeric leaflets. However, the valve may incorporate leaflets formed from natural tissues or from other materials.

As these and other variations and combinations of the features discussed above can be utilized without departing from the present invention, the foregoing discussion of the preferred embodiments should be taken by way of illustration rather than by way of limitation of the invention as defined by the claims.

The invention claimed is:

1. A method of making an implantable valve, the method comprising:
    (a) placing a mandrel having leaflet-forming surfaces into a stent having spaced-apart elongated leaflet support members so that the leaflet support members of the stent extend along ledges of the mandrel, each of the ledges extending from a main surface of the mandrel inwardly towards leaflet-forming surfaces of the mandrel spaced from the main surface, each of the ledges having an outer edge intersecting the main surface and each of the ledges having an inner edge opposite the outer edge and intersecting a proximal end of the leaflet-forming surfaces, the leaflet support members having openings therein;
    (b) depositing a flowable composition on the mandrel and the stent so that the flowable composition forms layers on the leaflet-forming surfaces spanning between the leaflet support members, contacts the leaflet support members and penetrates into the openings of the leaflet support members;
    (c) curing the flowable composition to a flexible solid so as to form leaflets extending between the leaflet support members, the leaflets being secured to the leaflet support members at least in part by the cured composition in the openings; and
    (d) removing the stent and the leaflets from the mandrel.
2. The method as claimed in claim 1, wherein the flowable composition covers a proximal section of the stent offset in a proximal direction from the leaflet support members so that the cured composition forms a cuff integral with the leaflets and covering at least a part of the proximal section.

3. The method as claimed in claim 1, further comprising aligning the main surface of the mandrel offset in a proximal direction from the leaflet-forming surfaces with a proximal section of the stent and aligning the leaflet-forming surfaces with valleys defined by the leaflet support members.

4. The method as claimed in claim 1, wherein the stent has collapsed and expanded conditions and the mandrel is placed into the stent while the stent is in the expanded condition.

5. The method as claimed in claim 1, further comprising trimming the cured composition along edges of the leaflet-forming surfaces of the mandrel.

6. A method of making an implantable valve, the method comprising:
    (a) placing a mandrel having leaflet-forming surfaces into a stent having spaced-apart elongated leaflet support members so that the leaflet support members of the stent extend along ledges of the mandrel, each of the ledges extending between a main surface of the mandrel and leaflet-forming surfaces of the mandrel spaced from the main surface, each of the ledges having an outer edge intersecting the main surface and each of the ledges having an inner edge opposite the outer edge and intersecting a proximal end of the leaflet-forming surfaces;
    (b) depositing a flowable composition on the mandrel and the stent so that the flowable composition spans between the leaflet support members;
    (c) curing the flowable composition so as to form leaflets extending between the leaflet support members; and
    (d) removing the stent and the leaflets from the mandrel.

7. The method as claimed in claim 6, wherein the flowable composition covers a proximal section of the stent offset in a proximal direction from the leaflet support members so that the cured composition forms a cuff integral with the leaflets and covering at least a part of the proximal section.

8. The method as claimed in claim 6, further comprising aligning the main surface of the mandrel offset in a proximal direction from the leaflet-forming surfaces with a proximal section of the stent and aligning the leaflet-forming surfaces with valleys defined by the leaflet support members.

9. The method as claimed in claim 8, wherein at least a first one of the ledges extends along and intersects with an entirety of a proximal edge of one of the leaflet-forming surfaces and one of the leaflet support members extends along and has a substantially similar curvature to the first one of the ledges.

10. The method as claimed in claim 6, wherein the ledges do not intersect each other.

11. The method as claimed in claim 6, wherein the mandrel further comprises a step extending from edges at distal sides of each of the leaflet-forming surfaces such that the edges are free edges, the ledges extending to proximal sides of the leaflet-forming surfaces.

12. The method as claimed in claim 11, wherein the mandrel further comprises a neck portion intersecting the step and a forward portion directly attached to the neck portion, the step of the mandrel extends inwardly towards a central axis of the mandrel, and the forward portion has a cross-sectional shape similar to a collective shape of the leaflet-forming surfaces, a thickness of the forward portion extending outwardly away from the central axis of the mandrel.

13. The method as claimed in claim 6, wherein the stent has collapsed and expanded conditions and the mandrel is placed into the stent while the stent is in the expanded condition.

14. The method as claimed in claim 6, wherein the composition includes at least one polymer and a solvent and the curing step includes removing the solvent from the composition.

15. The method as claimed in claim 6, wherein the composition includes a polymer and a solvent and the curing step includes absorbing the solvent into the polymer.

16. The method as claimed in claim 6, wherein the composition includes chemically-reactive moieties including a polymer and the curing step includes mixing the chemically-reactive moieties.

17. The method as claimed in claim 6, further comprising trimming the cured composition along edges of the leaflet-forming surfaces of the mandrel.

18. The method as claimed in claim 6, wherein the flowable composition includes a material selected from the group comprising polyurethanes, polyurethane-silicone copolymers, poly(styrene-b-isobutylene-b-styrene), polydimethyl siloxanes, and polytetrafluoroethylenes.

19. The method as claimed in claim 6, wherein the flowable composition includes a material selected from the group comprising collagen, elastin, silk, keratin, gelatin, polyamino acids, and polysaccharides.

20. A method of making an implantable valve, the method comprising:
(a) placing a mandrel having leaflet-forming surfaces into a stent having spaced-apart elongated leaflet support members so that a main surface of the mandrel offset in a proximal direction from the leaflet-forming surfaces is aligned with a proximal section of the stent and so that the leaflet support members of the stent are aligned with the leaflet-forming surfaces of the mandrel, the leaflet support members having openings therein;
(b) depositing a flowable composition on the mandrel and the stent so that the flowable composition forms a film on the leaflet-forming surfaces that spans between the leaflet support members, contacts the leaflet support members, penetrates into the openings of the leaflet support members, and covers the proximal section of the stent offset in the proximal direction from the leaflet support members;
(c) curing the flowable composition to a flexible solid so as to form leaflets extending between the leaflet support members and so as to form a cuff integral with the leaflets and covering at least a part of the proximal section, the leaflets being secured to the leaflet support members at least in part by the cured composition in the openings;
(d) trimming the cured composition along free edges at distal sides of each of the leaflet-forming surfaces of the mandrel; and
(e) removing the stent and the leaflets from the mandrel, wherein the mandrel comprises:
a step extending from the free edges at the distal sides of each of the leaflet-forming surfaces of the mandrel and inwardly towards a central axis of the mandrel;
a neck portion intersecting the step; and
a forward portion directly attached to the neck portion, having a cross-sectional shape similar to a collective shape of the leaflet-forming surfaces, and having a thickness extending outwardly away from the central axis of the mandrel.

\* \* \* \* \*